United States Patent
Blate et al.

(10) Patent No.: US 12,015,852 B2
(45) Date of Patent: Jun. 18, 2024

(54) DOCTOR-PATIENT VIDEO INTERFACE DEVICE

(71) Applicant: AURA Technologies, LLC, Chapel Hill, NC (US)

(72) Inventors: Alex Blate, Chapel Hill, NC (US); Douglas Bennett, Chapel Hill, NC (US); Anna Bennett, Chapel Hill, NC (US); Garrett Goss, Morrisville, NC (US)

(73) Assignee: AURA Technologies, LLC, Carrboro, NC (US)

( * ) Notice: Subject to any disclaimer, the term of this patent is extended or adjusted under 35 U.S.C. 154(b) by 0 days.

(21) Appl. No.: 17/960,094

(22) Filed: Oct. 4, 2022

(65) Prior Publication Data

US 2023/0119352 A1  Apr. 20, 2023

Related U.S. Application Data

(63) Continuation of application No. PCT/US2021/027185, filed on Apr. 14, 2021.
(Continued)

(51) Int. Cl.
*G06F 1/16* (2006.01)
*G16H 40/67* (2018.01)
(Continued)

(52) U.S. Cl.
CPC .......... *H04N 23/695* (2023.01); *G16H 40/67* (2018.01); *G16H 80/00* (2018.01); *B62B 3/00* (2013.01)

(58) Field of Classification Search
None
See application file for complete search history.

(56) References Cited

U.S. PATENT DOCUMENTS

| 2003/0052787 A1 | 3/2003 | Zerhusen et al. |
| 2007/0115355 A1* | 5/2007 | McCormack .......... H04N 7/185 348/E5.042 |

(Continued)

OTHER PUBLICATIONS

International Search Report for PCT/US2021/027185, Jul. 19, 2021, 2 pages.
Written Opinion for PCT/US2021/027185, Jul. 19, 2021, 5 pages.

*Primary Examiner* — Edemio Navas, Jr.
(74) *Attorney, Agent, or Firm* — Danielson Legal LLC

(57) ABSTRACT

A video interface device, the device including a camera; an optically transparent enclosure, the enclosure configured to enclose the camera and configured for sanitization; a height-adjustable mount connected to the optically transparent enclosure; a computer display connected to the height-adjustable mount; and a cart connected to the height-adjustable mount, wherein the camera and the computer display are configured to facilitate communication with at least one remote system. A method of constructing a video interface device, including enclosing a first camera in an optically-transparent enclosure, the enclosure being configured for sanitization; attaching the first camera in the optically-transparent enclosure to a height-adjustable mount; attaching a computer display to the height-adjustable mount; and attaching a cart to the height-adjustable mount, such that the first camera and the computer display are configured to facilitate communication with at least one remote system.

24 Claims, 9 Drawing Sheets

Related U.S. Application Data

(60) Provisional application No. 63/009,535, filed on Apr. 14, 2020.

(51) Int. Cl.
*G16H 80/00* (2018.01)
*H04N 23/695* (2023.01)
*B62B 3/00* (2006.01)

(56) References Cited

U.S. PATENT DOCUMENTS

| | | | |
|---|---|---|---|
| 2012/0102434 A1* | 4/2012 | Zerhusen | G16H 40/20 715/835 |
| 2013/0286353 A1* | 10/2013 | Steinmetz | G06V 40/67 351/245 |
| 2014/0135990 A1* | 5/2014 | Stuart | H04L 65/403 700/259 |
| 2014/0267715 A1* | 9/2014 | Kemege | G08B 13/19632 348/143 |
| 2018/0247712 A1 | 8/2018 | Stuart et al. | |
| 2021/0152739 A1* | 5/2021 | Lu | H04N 5/783 |

* cited by examiner

DOCTOR-PATIENT VIDEO INTERFACE DEVICE

CROSS REFERENCE TO RELATED APPLICATIONS

The present application is a continuation of International (PCT) Patent Application No. PCT/US2021/027185, filed internationally on Apr. 14, 2021, and claims the benefit of and priority to U.S. provisional application No. 63/009,535, filed on Apr. 14, 2020, the entire disclosure of each of which is hereby incorporated by reference as if set forth in their entirety herein.

TECHNICAL FIELD

Embodiments described herein relate to methods and systems for applications of a video interface device and, more particularly but not exclusively, to methods and systems for height-adjustable devices with an optically transparent enclosure to enclose the camera and configured for sanitization.

BACKGROUND

Physicians and other health care providers may interact with patients remotely, for example, due to geographic separation or avoiding the transmission of infectious diseases. This is part of the growing field sometimes referred to as "telemedicine." Video conferencing and video chat software and hardware are often used to facilitate these remote interactions, often using off-the-shelf digital video cameras ("webcams"), laptops, microphones and speakers, smartphones, etc. Video provides some additional degree of presence compared to an audio-only interaction which can make the experience feel more personal and comfortable for the patient.

In many areas of medicine, physicians rely on visual examinations or observations of patients. For example, physicians may need to carefully observe a patient's eyes during certain neurological exams. In hospital settings, the patient may be laying down or reclined, making use of typical off-the-shelf computer or webcam configurations difficult. In some cases, if the patient is comatose or heavily sedated, the patient himself may not be able to directly participate.

When telemedicine hardware is shared between patients (e.g., during remote "rounds"), and particularly if the patient must physically touch parts of the hardware, then disinfection is required to ensure that the telemedicine hardware is not a disease transmission vector. Permanent installation of cameras in each patient room may be prohibited in some jurisdictions, may raise privacy concerns, and may be too costly.

A need therefore exists for methods and systems to improve video interfaces and the facilitation of telemedicine.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

According to one aspect, embodiments relate to a video interface device. In some embodiments, the video interface device includes a camera; an optically transparent enclosure, the enclosure configured to enclose the camera and configured for sanitization; a height-adjustable mount connected to the optically transparent enclosure; a computer display connected to the height-adjustable mount; and a cart connected to the height-adjustable mount, wherein the camera and the computer display are configured to facilitate communication with at least one remote system.

In some embodiments, the camera is positioned above the computer display.

In some embodiments, the camera is a pan-tilt-zoom camera having at least one remotely controlled, motorized actuator configured to adjust the orientation of the camera.

In some embodiments, the communication is wireless.

In some embodiments, the video interface device further includes at least one audio input component and at least one audio output component.

In some embodiments, the height-adjustable mount is configured to be manually adjusted.

In some embodiments, the video interface device further includes a portable power source.

In some embodiments, the display is a touch screen.

In some embodiments, the video interface device further includes a second camera.

In some embodiments, the optically transparent enclosure is configured to be transparent over at least 180 degrees.

In some embodiments, the enclosure is an optically transparent dome.

In another aspect, embodiments relate to a method of constructing a video interface device. In some embodiments, the method includes enclosing a first camera in an optically transparent enclosure, the enclosure being configured for sanitization; attaching the first camera in the optically transparent enclosure to a height-adjustable mount; attaching a computer display to the height-adjustable mount; and attaching a cart to the height-adjustable mount, such that the first camera and the computer display are configured to facilitate communication with at least one remote system.

In some embodiments, the method further includes positioning the first camera above the computer display.

In some embodiments, the first camera is a pan-tilt-zoom camera having at least one remotely controlled, motorized actuator configured to adjust the orientation of the first camera.

In some embodiments, the communication is wireless.

In some embodiments, the method further includes attaching at least one audio input component and at least one audio output component to the video interface device.

In some embodiments, the height-adjustable mount is configured to be manually adjusted.

In some embodiments, the video interface device is configured to be powered by a portable power source.

In some embodiments, the method further includes attaching a second camera to the video interface device.

In some embodiments, the movement and focus of the second camera and the first camera are independently controllable.

In some embodiments, the optically transparent enclosure has an optically opaque top.

In some embodiments, the optically transparent sanitary enclosure is configured to be transparent over at least 180 degrees.

In another aspect, embodiments relate to a method of using a video interface device to view a patient. In some embodiments, the method includes positioning the video interface device in close proximity to the patient, the patient located on a piece of furniture; adjusting the location of the camera in the optically-transparent enclosure, such that the camera is located over the patient and at least a section of the cart is located under the piece of furniture; and adjusting at least one of the position of the piece of furniture, configuration of the piece of furniture, or the pan, tilt, or zoom of the camera, such that a user can remotely view the patient with the at least one remote system.

In some embodiments, the method further includes automatically aligning the camera such that the focal center of a view of the camera is perpendicular to the face of the patient.

BRIEF DESCRIPTION OF DRAWINGS

Non-limiting and non-exhaustive embodiments of this disclosure are described with reference to the following figures, wherein like reference numerals refer to like parts throughout the various views unless otherwise specified.

DETAILED DESCRIPTION

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

Embodiments described herein relate to doctor-patient video interface devices that can be easily disinfected and methods of using the interface devices. In some embodiments, the device has at least one camera surrounded by an optically transparent sanitary enclosure. The sanitary enclosure may be partially transparent or may be fully transparent in some embodiments. The device may also have a separate computer display or monitor. In some embodiments, the device may be mounted on a wheeled cart or stand and may have a height-adjustable mount for both the computer display and the camera surrounded by the enclosure. In some embodiments, the entire device may be configured to be disinfected with a standard disinfectant, such as a spray, UV, or aerosol because there are no "difficult to reach" areas (such as crevices, cracks, open seams, etc.). In some embodiments, the enclosure may be attached to the height-adjustable mount so that it encloses the camera without restricting the camera's range of movement or occluding its vision. The device may be connected, possibly wirelessly, to a computer, network, or digital system. The system may use battery power or a plug-in power source. The camera and display may have adjustable pan, tilt and/or zoom features and a user may remotely control these features.

Figure 1B:
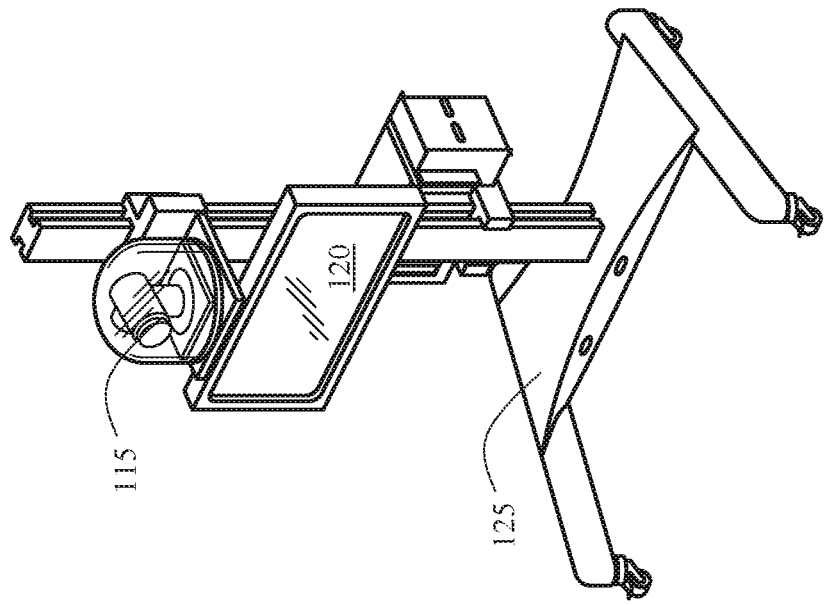
FIG. 1B depicts the video interface device of FIG. 1A in a lowered position.
Figure 1A:
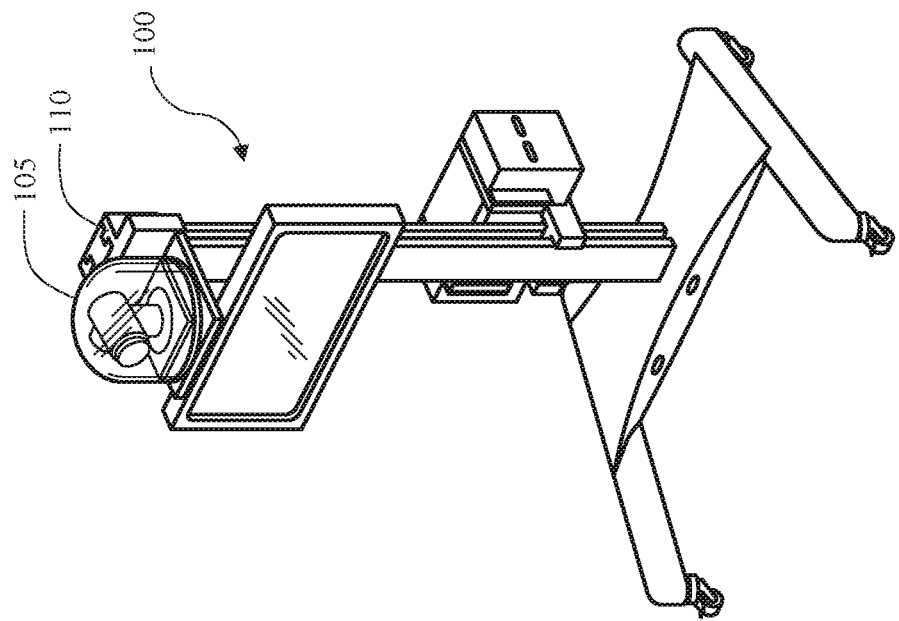
FIG. 1A depicts a video interface device with an optically transparent enclosure and height-adjustable mount in accordance with one embodiment.

FIG. 1A depicts a video interface device 100 with an optically transparent enclosure 105 and height-adjustable mount 110 in accordance with one embodiment and FIG. 1B depicts the video interface device 100 of FIG. 1A in a lowered position.

In some embodiments, the device 100 comprises a camera 115, an optically transparent enclosure 105, a display 120, a cart 125, and height-adjustable mount 110. In some embodiments, the camera 115 is digital. In some embodiments, the camera 115 is a webcam. In some embodiments, the display 120 is a computer display or monitor. In some embodiments, the cart 125 is a wheeled cart or stand.

In some embodiments, the height-adjustable mount 110 is attached to the cart 125 and the display 120. In some embodiments, the camera 115 is attached to the height-adjustable mount 110 such that it is positioned above the display 120. In some embodiments, the optically transparent enclosure 105 is attached to the height-adjustable mount 110 such that it encloses the camera 115 without restricting the camera's range-of-movement or occluding its vision.

In some embodiments, the distance between the camera 115 and the display 120 remains constant throughout the range of adjustment of the height-adjustable mount 110. In some embodiments, the height-adjustable mount 110, the enclosure 105, and the camera 115 are arranged such that light from behind and/or above the camera 115 is blocked. In some embodiments, blocking light from behind and/or above the camera 115 avoids glare or reflections from the enclosure 105.

In some embodiments, the camera 115 is a pan-tilt-zoom (PTZ) camera. In some embodiments, the camera 115 has remotely controlled, motorized adjustments/actuators for pan (yaw), tilt (pitch), and zoom (focal length of lens). In some embodiments, at least one of the pan, tilt, or zoom functions of the camera 115 can be controlled by the patient. In some embodiments, a doctor or other medical professional can remotely control the functions of the camera 115.

Figures 2A, 2B:
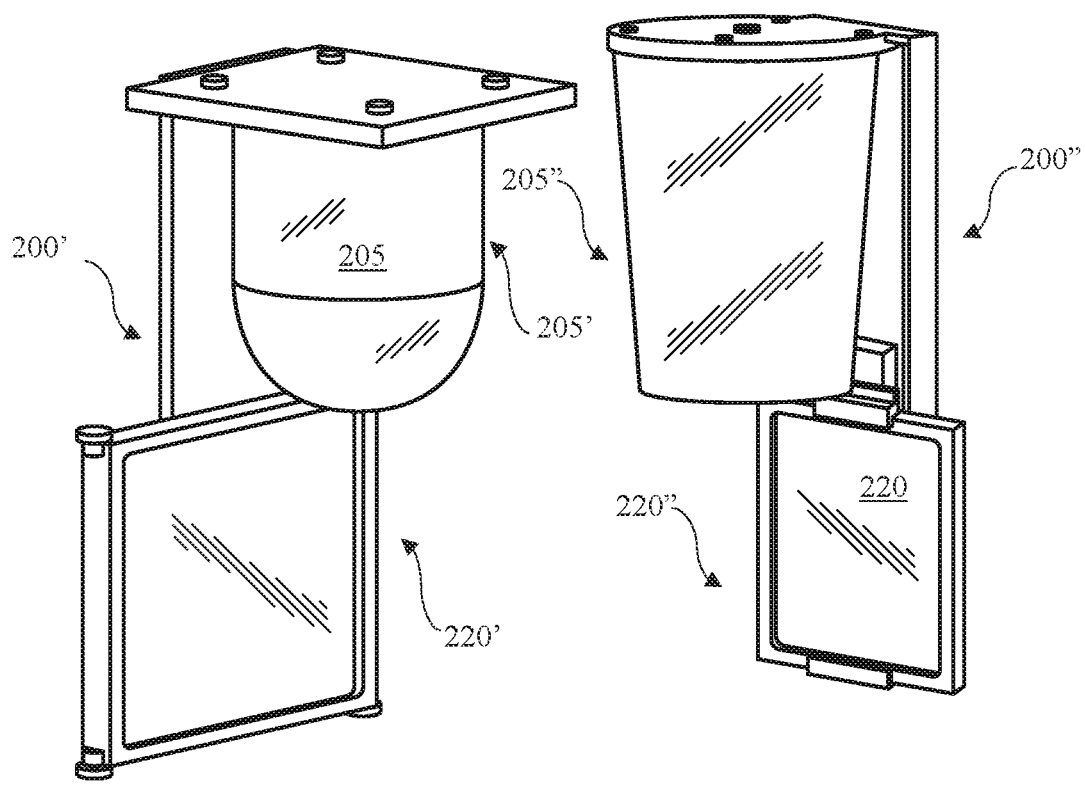
FIG. 2A depicts a video interface device with an optically transparent enclosure in accordance with one embodiment.
FIG. 2B depicts a video interface device with an optically transparent enclosure in accordance with another embodiment.

FIG. 2A and FIG. 2B depict video interface devices 200', 200" (collectively 200) with an optically transparent enclosure 205', 205" (collectively 205) in accordance with some embodiments.

In some embodiments, the enclosure 205 is designed such that it can easily and non-destructively be cleaned with disinfectants and cleaning agents in common use for the disinfection of portable electronic medical equipment. These disinfectants and cleaning agents may include any combination of aqueous solutions containing soaps, detergents, anti-microbial substances, and denatured alcohol, such as isopropanol, ethanol, or methanol. In some embodiments, the surface of the display 220', 220" (collectively 220) and all other accessible surfaces of the device 200 can be cleaned and/or disinfected in like manner.

In some embodiments, the enclosure 205 may be an optically transparent dome. In some embodiments, the enclosure 205 may be any substantially convex, optically transparent shape that accommodates a camera (not shown) and the camera's range of pan and tilt over a requisite field of view. For example, the enclosure 205 may be at least one of sphere-shaped, cylindrically shaped, or a spheroid of non-constant radius.

In some embodiments, the enclosure 205 may comprise one or more anti-scratch, anti-glare/reflection, or other coatings. In some embodiments, the enclosure 205 may have at least one optically transparent component that is field-replaceable using simple hand tools.

Figure 3:
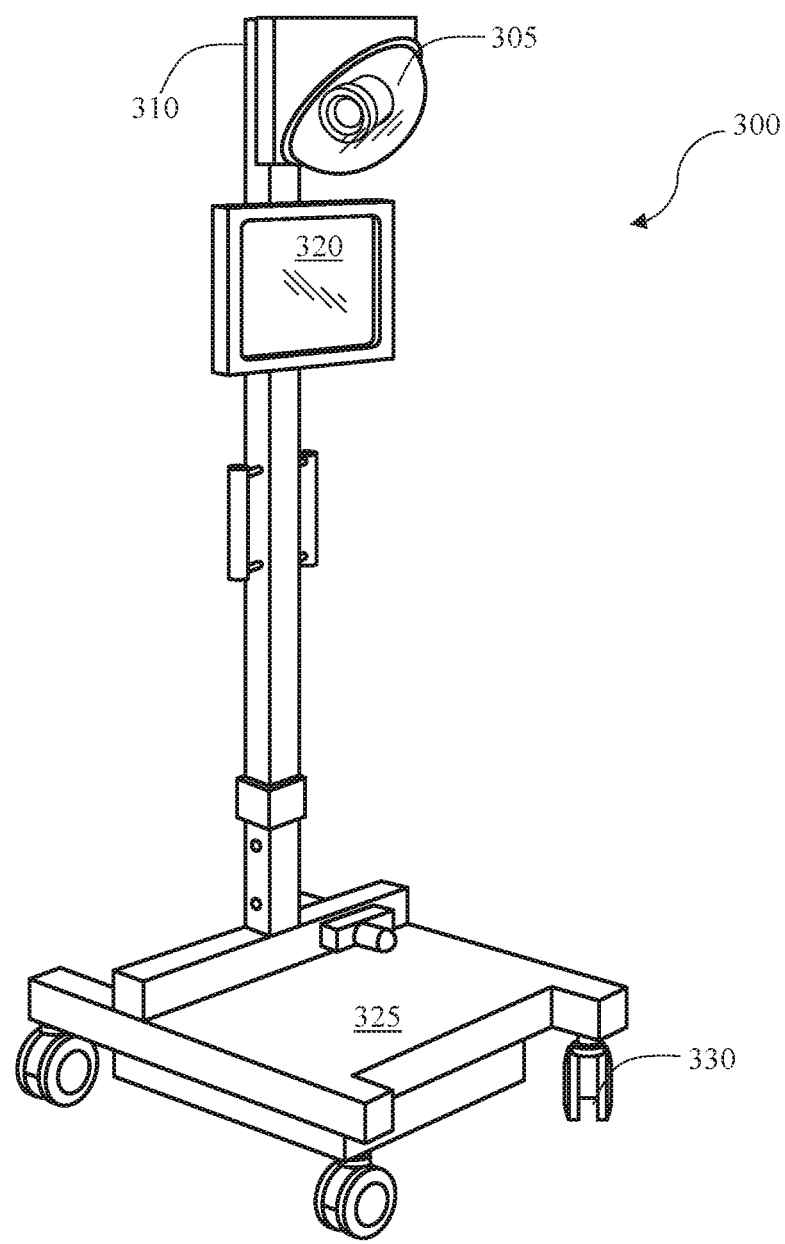
FIG. 3 depicts a video interface device with an optically transparent enclosure and height-adjustable mount in accordance with one embodiment.

FIG. 3 depicts a video interface device 300 with an optically transparent enclosure 305 and height-adjustable mount 310 in accordance with one embodiment. In some embodiments, the device 300 may comprise a display 320 configured to present information or conference with a user or operator. In some embodiments, the display 320 is a touch-screen display, such that all normal system operations can be controlled or performed via the touchscreen. In some embodiments, the touchscreen is designed such that it functions correctly when the operator is wearing protective gloves and when the operator is not wearing gloves.

In some embodiments, the video interface device 300 may be coupled to a cart 325. In some embodiments, a cart 325 comprises any object having at least one of wheels or casters 330.

Figure 4:
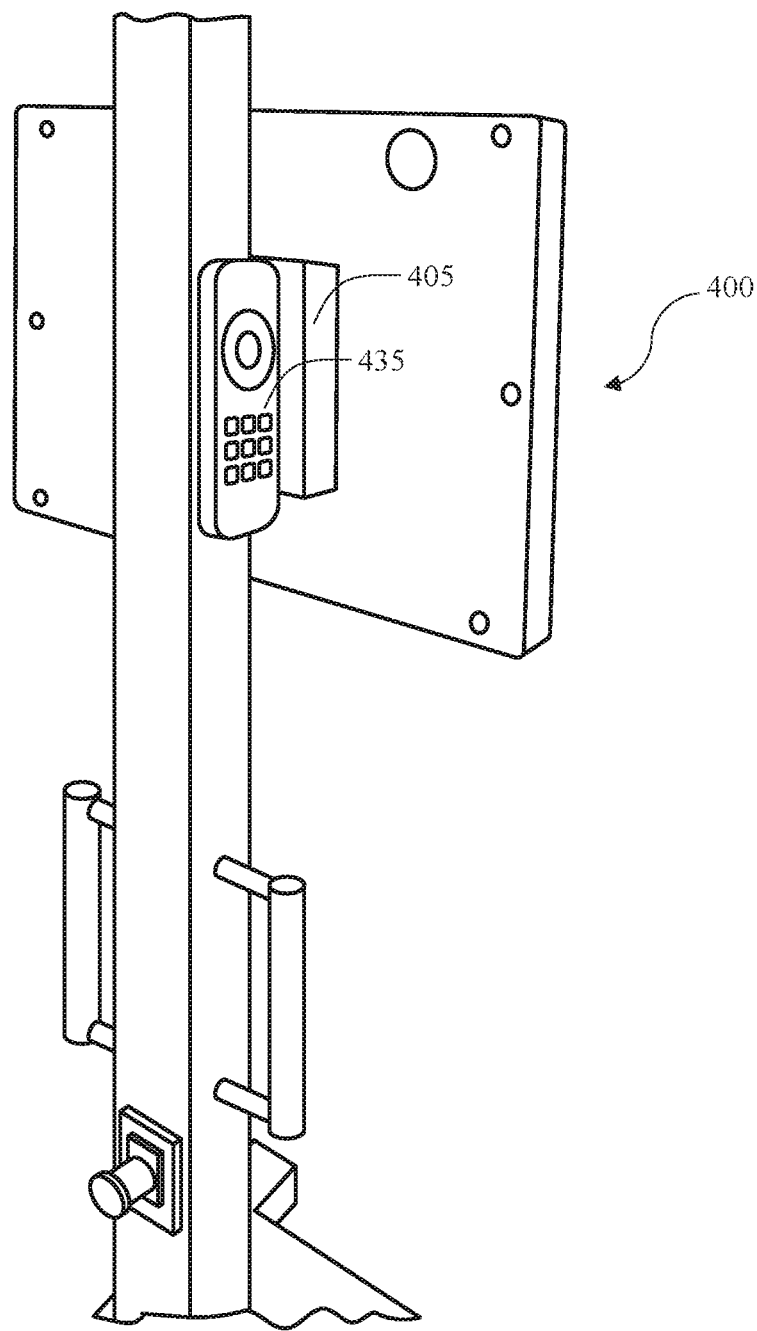
FIG. 4 depicts a video interface device with a height-adjustable mount and controller in accordance with one embodiment.

FIG. 4 depicts a video interface device 400 with a height-adjustable mount 405 and controller 435 in accordance with one embodiment.

In some embodiments, the camera and display are connected to a computer which, in some embodiments, is attached to the cart or height-adjustable mount. In some embodiments, the display is part of a tablet computer, 2-in-1 laptop/tablet computer, all-in-one computer, or equivalent; in these cases, the camera connects to the display (which itself is also a computer).

The camera and display shown in FIG. 1A and FIG. 3 (not shown in FIG. 4) may be connected to one or more computers, computer networks, or other digital systems facilitating communication with one or more remote systems. Typically, communication between the apparatus and remote systems is via a wireless network or wireless connection. In some embodiments, communication between the apparatus and remote systems is via a wired network. Typically, the device further comprises audio input and output components, e.g., speaker(s) and microphone(s).

Figure 5:
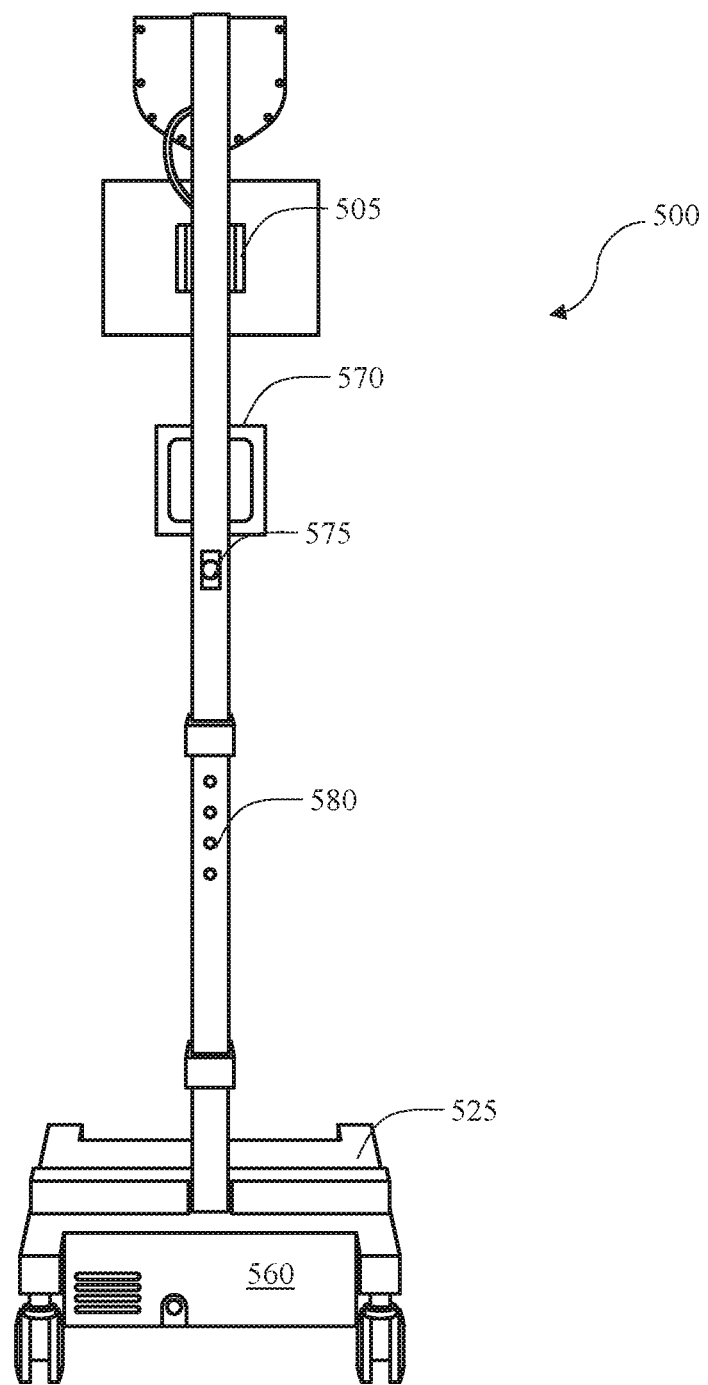
FIG. 5 depicts a video interface device with a height-adjustable mount on a cart in accordance with one embodiment.

FIG. 5 depicts a video interface device 500 with a height-adjustable mount 505 on a cart 525 in accordance with one embodiment.

In some embodiments, the device 500 comprises a portable power source 560, such as a battery pack or an uninterruptable power supply, such that the device 500 can be operated without a mains power connection for some period of time. In some embodiments, all components of the device 500 operate at low-voltage DC (e.g., 48 Volts or lower) for safety and mains-powered battery charging equipment is external to the apparatus. In some embodiments, the device 500 can be powered from mains and/or recharged while in use/operation.

In some embodiments, the cart 525 is a wheeled cart. In some embodiments, the wheeled cart 525 is replaced by a stand allowing the device 500 to be placed on a table or desk. In some embodiments, the device 500 further comprises one or more handles 570 for safely transporting the device 500. In some embodiments, a user can move the device 500 by pulling on at least one handle 570.

In some embodiments, the height-adjustable mount 505 is adjusted manually. In some embodiments, the height-adjustable mount 505 is powered/motorized and can be adjusted remotely and/or without touching the device 500. Some embodiments may incorporate a locking mechanism 575 to prevent accidental or unauthorized vertical movement/adjustment of the height-adjustable mount 505. In some embodiments, the height-adjustable mount 505 may use a ratchet system 580, such that there are set intervals to adjust the height of the device 500. In some embodiments, the height-adjustable mount 505 may be continuously adjustable.

Figure 6:
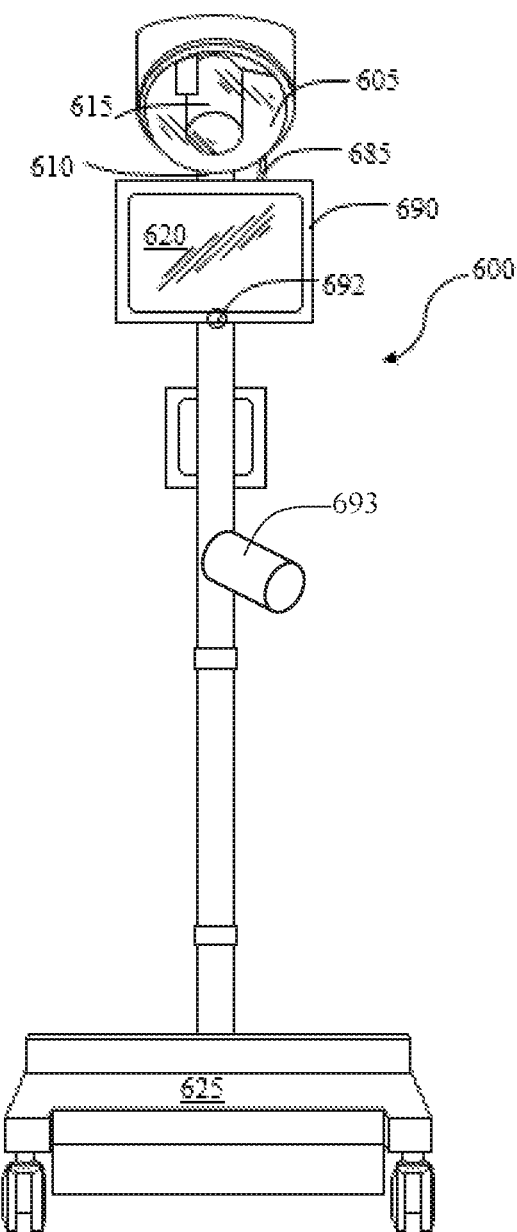
FIG. 6 depicts a video interface device with an optically transparent enclosure and height-adjustable mount on a cart in accordance with one embodiment.

FIG. 6 depicts a video interface device 600 with an optically transparent enclosure 605 and height-adjustable mount 610 on a cart 625 in accordance with one embodiment.

In some embodiments, the camera 615 is attached to the enclosure 605 and the enclosure 605 is attached to the mount 610. In some embodiments, the exact point where the enclosure 605 ends and the mount 610 begins is not critical as long as the camera 615 is fully enclosed within the enclosure 605.

In some embodiments, the video interface device 600 is connected 685 to a computer 690. In some embodiments, the computer 690 is associated with the display 620. In some embodiments, the computer 690 is a separate entity from the display 620 (not shown). In some embodiments, the computer 690 is not physically attached to the cart 625. In some embodiments, computer 690 is configured to execute software facilitating communication from the device 600 to a remote system. In some embodiments, the display 620 is a touch screen and has controls, such that a user interacting with the controls on the touch screen can control at least some aspects of the device 600 and can provide input to the computer 690.

In some embodiments, the device 600 comprises a privacy mechanism (not shown), such as a movable opaque cover or curtain that blocks the camera 615.

In some embodiments, the device 600 can be easily sanitized and/or disinfected. In some embodiments, sanitization comprises the ability to sanitize or disinfect the entire exterior surface of the video interface device 600, including the cart 625 and the optically transparent enclosure 605 with cleaning substances known to someone of ordinary skill in the art. In some embodiments, the camera 615 may not need to be disinfected because it is surrounded by the protective enclosure 605. In some embodiments, camera 615 itself is not able to be sanitized or disinfected (easily or at all) over its entire exterior surface. In some embodiments, the sanitary enclosure 605 facilitates the use of such cameras in sanitary settings, e.g., health care facilities. In some embodiments, the cleaning substances may include rubbing alcohol, including any aqueous solution where a majority of the volume comprises at least one of denatured ethanol, isopropanol, or methanol; dilute bleach, including an aqueous solution of sodium hypochlorite, typically 3% concentration; and aqueous surface disinfectant (e.g., those typically used in health care contexts).

In some embodiments, the device 600 comprises a second camera 692 or a handheld camera 693 with macro focus; the handheld camera 693 may be wired or wireless. The handheld camera 693 may be operated by a nurse, physician's assistant, or other user of the device 600. In some embodiments, the handheld camera 693 is configured to enable a remote user, such as a remote physician, to see views of the patient's body (such as for inspecting a wound) that would be difficult or impossible to view using the camera 615 and/or which require closer focus or magnification. In some embodiments, the handheld camera 693 may be installed within a sanitary enclosure. In some embodiments, the sanitary disclosure may be disposable or reusable. In some embodiments, the handheld camera 693 may be sanitized or disinfected directly without damage to the camera 693. In some embodiments, the handheld camera 693 may also be used for sharing documents, charts, or other items visually with a user on the display 620. In some embodiments, the handheld camera 693 may be magnetically-retained or mounted on the cart 625.

Figure 7:
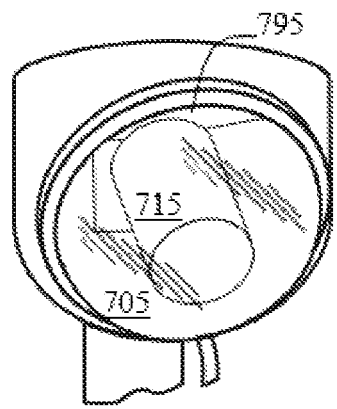
FIG. 7 depicts a camera with an optically transparent enclosure and an optically opaque top in accordance with one embodiment.

FIG. 7 depicts a camera 715 with an optically transparent enclosure 705 and an optically opaque top 795 in accordance with one embodiment. In some embodiments, only a portion of the optically transparent enclosure 705 is optically transparent. In some embodiments, the enclosure 705 is optically transparent in the view area of the camera 715 and opaque in other areas. In some embodiments, the optically transparent part of the enclosure 705 is made of any glass or plastic configured to be transparent; one of ordinary skill in the art will also understand that the transparent part of the enclosure 705 may be designed to avoid or minimize optical distortion or other factors affecting image quality or fidelity. In some embodiments, the remaining structure of the enclosure 705 may comprise non-transparent materials such as metal or opaque plastic. In some embodiments, the top 795 of the enclosure is opaque. In some embodiments, the top 795 of the enclosure is at least optically translucent. In some embodiments, the top 795 of the enclosure is a dark color. In some embodiments, an opaque top 795 or other top that is not optically transparent is configured to reduce glare or other interference from overhead lighting.

Figure 8:
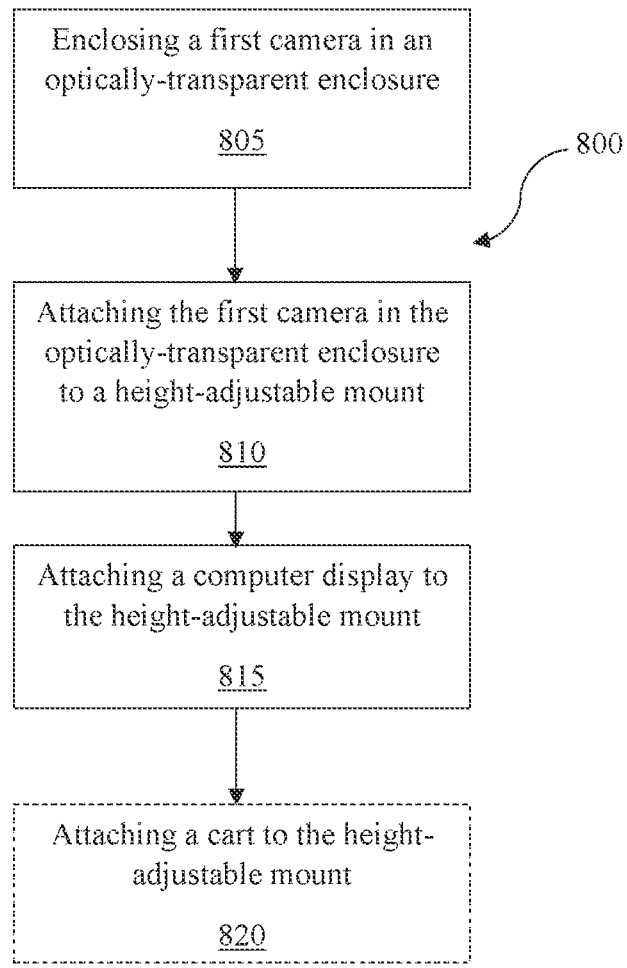
FIG. 8 illustrates a method of constructing a video interface device in accordance with one embodiment.

FIG. 8 illustrates a method 800 of constructing a video interface device in accordance with one embodiment. In some embodiments, the method 800 comprises enclosing a first camera in an optically transparent enclosure 805, attaching the first camera in the optically transparent enclosure to a height-adjustable mount 810, and attaching a computer display to the height-adjustable mount 815. In some embodiments, the method 800 comprises attaching a cart to the height-adjustable mount 820. In some embodiments, instead of attaching a cart to the height-adjustable mount 820, the method includes attaching a table or stand to the height-adjustable mount. In some embodiments, the optically transparent enclosure is partially optically transparent, such that the camera within the enclosure has a full vision range and the enclosure is configured to prevent glare from light surrounding the camera and enclosure.

Figure 9:
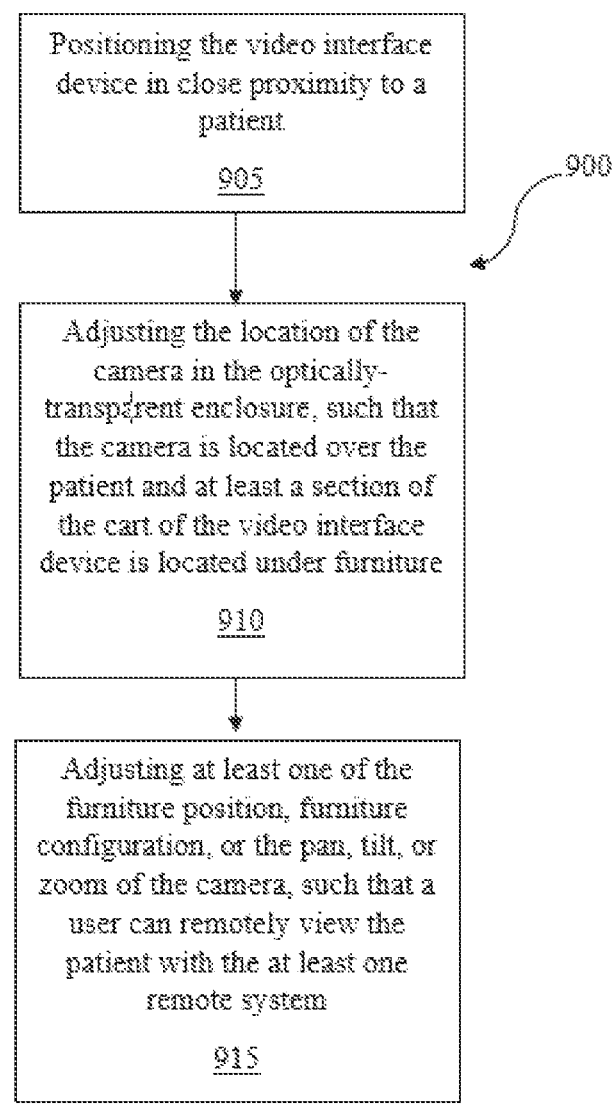
FIG. 9 illustrates a method of using a video interface device in accordance with one embodiment.

FIG. 9 illustrates a method 900 of using a video interface device in accordance with one embodiment. In some embodiments, the method comprises positioning the video interface device in close proximity to the patient 905, the patient located on a piece of furniture. In some embodiments, the piece of furniture may be a bed or a chair. In some embodiments, the method further comprises adjusting the location of the camera in the optically transparent enclosure, such that the camera is located over the patient and at least a section of the cart of the video interface device is located under the piece of furniture 910. In some embodiments, the method further comprises adjusting at least one of the furniture position, furniture configuration, or the pan, tilt, or zoom of the camera, such that a user can remotely view the patient with the at least one remote system 915.

In some embodiments, the location and orientation of the camera may be adjusted to view a patient in a bed. For example, in the context of a patient lying in a bed, at least one of the position of the cart, the height of the camera, and the camera's orientation (pan and tilt) can be adjusted such that the camera's optical axis intersects a reclined patient's face and is parallel with the medial (anterior posterior) axis of the reclined patient's head within ±20°, where the patient is reclined at an angle of less than or equal to 70°. In some embodiments, the camera is able to be aligned such that its view of the patient's face is off axis by at most 20° assuming that the patient's torso or the patient's head is inclined at least 20° above horizontal. In some embodiments, this adjustment may be done remotely. In some embodiments, the video interface device may be adjusted manually. In some embodiments, the video interface device may automatically adjust at least one of position, pan, or zoom of the camera to focus on a patient or a body part of a patient without user input.

In some embodiments, the camera may be aligned in a position that, when tilted down, the view from the camera is equivalent to the view of a doctor standing in front of or leaning over a patient (as opposed to off axis). In some embodiments, the camera may be aligned automatically, manually, or some combination thereof such that the focal center of the camera view is perpendicular to the face of the patient. In some embodiments, the wheels of the device may be under the bed of the patient, such that the camera can get a more direct view of the patient.

In some embodiments, the device may enable physicians to conduct visual examinations of patients in hospital beds at a level of detail and resolution sufficient for neurologists (e.g., such that the physician can observe fine eye movements). In some embodiments, the camera is positioned at the foot of the patient bed and the patient is inclined in the bed by ~20°. In some embodiments, the camera is raised to a height such that a user receiving the camera input has a direct view into the patient's face (roughly perpendicular to the frontal plane of the head or, equivalently, parallel to the sagittal/longitudinal plane of the head). In some embodiments, a user may be able to (optically) zoom in such that the patient's face and eyes are visible with sufficient detail. In some embodiments, the device has a relatively high optical zoom, pan/tilt, and the ability to adjust the height of the camera and display to achieve the desired geometry.

In some embodiments, the camera may be configured to be directly over the head or body of the patient, such that a patient lying in bed would not need to be tilted to be examined. In some embodiments, the range of adjustment of the height-adjustable mount can be set such that the camera is at eye-level for a seated adult. In some embodiments, the zoom function of the camera comprises an optical zoom function with sufficient magnification (focal length) that it can be zoomed in such that the patient's head occupies all of the horizontal and/or vertical field-of-view of the camera at a range of at least two (2) meters.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

What is claimed is:

1. A video interface device comprising:
    a camera;
    an optically transparent enclosure, the enclosure configured to enclose the camera and configured for sanitization;
    a height-adjustable mount connected to the optically transparent enclosure;
    a computer display connected to the height-adjustable mount and positioned below an optical axis of the camera, wherein a distance between the camera and the display always remains constant throughout a range of adjustment of the height-adjustable mount; and
    a cart connected to the height-adjustable mount, wherein the camera and the computer display are configured to facilitate communication with at least one remote system.

2. The video interface device of claim 1, wherein the camera is positioned above the computer display.

3. The video interface device of claim 1, wherein the camera is a pan-tilt-zoom camera having at least one remotely controlled, motorized actuator configured to adjust the orientation of the camera.

4. The video interface device of claim 1, wherein the communication is wireless.

5. The video interface device of claim 1, further comprising at least one audio input component and at least one audio output component.

6. The video interface device of claim 1, wherein the height-adjustable mount is configured to be manually adjusted.

7. The video interface device of claim 1, further comprising a portable power source.

8. The video interface device of claim 1, wherein the display is a touch screen.

9. The video interface device of claim 1, further comprising a second camera.

10. The video interface device of claim 1, wherein the optically transparent enclosure is configured to be transparent over at least 180 degrees.

11. The video interface device of claim 1, wherein the enclosure is an optically transparent dome.

12. A method of constructing a video interface device, the method comprising:
    enclosing a first camera in an optically transparent enclosure, the enclosure being configured for sanitization;
    attaching the first camera in the optically transparent enclosure to a height-adjustable mount;
    attaching a computer display to the height-adjustable mount and positioned below an optical axis of the first camera, wherein a distance between the camera and the display always remains constant throughout a range of adjustment of the height-adjustable mount; and
    attaching a cart to the height-adjustable mount, such that the first camera and the computer display are configured to facilitate communication with at least one remote system.

13. The method of claim 12, further comprising positioning the first camera above the computer display.

14. The method of claim 12, wherein the first camera is a pan-tilt-zoom camera having at least one remotely controlled, motorized actuator configured to adjust the orientation of the first camera.

15. The method of claim 12, wherein the communication is wireless.

16. The method of claim 12, further comprising attaching at least one audio input component and at least one audio output component to the video interface device.

17. The method of claim 12, wherein the height-adjustable mount is configured to be manually adjusted.

18. The method of claim 12, wherein the video interface device is configured to be powered by a portable power source.

19. The method of claim 12, further comprising attaching a second camera to the video interface device.

20. The method of claim 19, wherein the movement and focus of the second camera and the first camera are independently controllable.

21. The method of claim 12, wherein the optically transparent enclosure has an optically opaque top.

22. The method of claim 12, wherein the optically transparent sanitary enclosure is configured to be transparent over at least 180 degrees.

23. A method of using the video interface device of claim 1 to view a patient, the method comprising:
- positioning the video interface device in close proximity to the patient, the patient located on a piece of furniture;
- adjusting the location of the camera in the optically transparent enclosure, such that the camera is located over the patient and at least a section of the cart is located under the piece of furniture; and
- adjusting at least one of the position of the piece of furniture, configuration of the piece of furniture, or the pan, tilt, or zoom of the camera, such that a user can remotely view the patient with the at least one remote system.

24. The method of claim 23, further comprising automatically aligning the camera such that the focal center of a view of the camera is perpendicular to the face of the patient.

\* \* \* \* \*